(12) United States Patent
Parker et al.

(10) Patent No.: US 12,048,584 B2
(45) Date of Patent: Jul. 30, 2024

(54) METHOD OF USING MULTIPARAMETRIC IMAGING DATA TO DIAGNOSE DISEASE STATES AND TO MONITOR THEIR PROGRESSION

(71) Applicant: University of Rochester, Rochester, NY (US)

(72) Inventors: Kevin J. Parker, Rochester, NY (US); Jihye Baek, Rochester, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 0 days.

(21) Appl. No.: 17/649,429

(22) Filed: Jan. 31, 2022

(65) Prior Publication Data
US 2022/0249054 A1    Aug. 11, 2022

Related U.S. Application Data

(60) Provisional application No. 63/145,118, filed on Feb. 3, 2021.

(51) Int. Cl.
| | |
|---|---|
| A61B 8/14 | (2006.01) |
| A61B 8/00 | (2006.01) |
| A61B 8/08 | (2006.01) |

(52) U.S. Cl.
CPC .............. *A61B 8/14* (2013.01); *A61B 8/085* (2013.01); *A61B 8/466* (2013.01); *A61B 8/483* (2013.01)

(58) Field of Classification Search
CPC ........... A61B 8/14; A61B 8/085; A61B 8/466; A61B 8/483; A61B 8/5223
See application file for complete search history.

(56) References Cited

U.S. PATENT DOCUMENTS

| | | | | |
|---|---|---|---|---|
| 4,646,748 A | * | 3/1987 | Fujii | G01N 29/0609 600/441 |
| 2017/0168149 A1 | * | 6/2017 | Parker | G01S 7/52071 |
| 2020/0225347 A1 | * | 7/2020 | Parker | G01S 7/52071 |
| 2022/0249054 A1 | * | 8/2022 | Parker | A61B 8/466 |

OTHER PUBLICATIONS

Khairalseed et al., Real-time H-scan ultrasound imaging using a Verasonics research scanner, Ultrasonics, vol. 94, 2019, pp. 28-36, Issn 0041-624X.*
Khairalseed et al., Spatial Angular Compounding Technique for H-Scan Ultrasound Imaging, Ultrasound in Medicine & Biology, vol. 44, Issue 1, 2018, pp. 267-277, ISSN 0301-5629.*
Khairalseed et al., H-scan sensitivity to scattering size, Journal of Medical Imaging, vol. 4, Issue 4, 043501, Nov. 2017.*
Ridley, Eirk, Math functions add color, detail to ultrasound images, Clinical New, Ultrasound, Nov. 10, 2016, https://www.auntminnie.com/clinical-news/ultrasound/article/15616252/math-functions-add-color-detail-to-ultrasound-images.*

(Continued)

*Primary Examiner* — Bo Joseph Peng
(74) *Attorney, Agent, or Firm* — Ping Wang; Kalos Athena Wang PLLC

(57) ABSTRACT

An ultrasound study in which the reflected echoes are analyzed to determine a physical characteristic of scatterers within the volume of interest, the acoustic attenuation within the volume of interest, and the echo amplitude. These data are used to diagnose the disease state and the progression of disease.

7 Claims, 3 Drawing Sheets
(3 of 3 Drawing Sheet(s) Filed in Color)

(56) References Cited

OTHER PUBLICATIONS

Willocks J, Donald I, Duggan TC, Day N. Foetal cephalometry by ultrasound. The Journal of obstetrics and gynaecology of the British Commonwealth 71, 11-20 (1964).
Thompson HE, Holmes JH, Gottesfeld KR, Taylor ES. Fetal development as determined by ultrasonic pulse echo techniques. American journal of obstetrics and gynecology 92, 44-52 (1965).
Häggström M. Medical gallery of Mikael Häggström 2014 (public domain). WikiJournal of Medicine 1, DOI: 10.15347/wjm/12014. 15008 (2014).
Schreiber S, et al. Quantifying disease progression in amyotrophic lateral sclerosis using peripheral nerve sonography. Muscle & nerve 54, 391-397 (2016).
Hung OY, et al. Comprehensive assessment of coronary plaque progression with advanced intravascular imaging, physiological measures, and wall shear stress: a pilot couble-blinded randomized controlled clinical trial of nebivolol versus atenolol in honobstructive coronary artery disease. J Am Heart Assoc 5, e002764 (2016).
Steffen BT, et al. Apolipoprotein B is associated with carotid atherosclerosis progression independent of individual cholesterol measures in a 9-year prospective study of Multi-Ethnic Study of Atherosclerosis participants. J Clin Lipidol 11, 1181-1191.e1181 (2017).
Zaidman CM, et al. Quantitative muscle ultrasound detects disease progression in Duchenne muscular dystrophy. Ann Neurol 81, 633-640 (2017).
Magistroni R, Corsi C, Marti T, Torra R. A review of the imaging techniques for measuring kidney and cyst volume in establishing autosomal fominant polycystic didney disease progression. Am J Nephrol 48, 67-78 (2018).
Dimcevski G, et al. A human clinical trial using ultrasound and microbubbles to enhance gemcitabine treatment of inoperable pancreatic cancer. J Control Release 243, 172-181 (2016).
Morales-Roselló J, et al. Progression of Doppler changes in early-onset small for gestational age fetuses. How frequent are the different progression sequences? J Matern Fetal Neonatal Med 31, 1000-1008 (2018).
Sacchi S, et al. Doppler assessment of aortic stenosis: a 25-operator study demonstrating why reading the peak velocity is superior to velocity time integral. Eur Heart J Cardiovasc Imaging 19, 1380-1389 (2018).
Doris MK, Everett RJ, Shun-Shin M, Clavel MA, Dweck MR. The role of imaging in measuring disease progression and assessing novel therapies in aortic stenosis. JACC Cardiovasc Imaging 12, 185-197 (2019).
Sadeghi-Naini A, et al. Chemotherapy-response monitoring of breast cancer patients using quantitative ultrasound-based intra-tumour heterogeneities. Sci Rep 7, 10352 (2017).
Li F, et al. Early differentiating between the chemotherapy responders and honresponders: preliminary results with ultrasonic spectrum analysis of the RF time series in preclinical breast cancer models. Cancer Imaging 19, 61 (2019).
Baek J, Ahmed R, Ye J, Gerber SA, Parker KJ, Doyley MM. H-scan, Shear Wave and Bioluminescent Assessment of the Progression of Pancreatic Cancer Metastases in the Liver. Ultrasound Med Biol 46, 3369-3378 (2020).
Baek J, Poul SS, Swanson TA, Tuthill T, Parker KJ. Scattering Signatures of Normal versus Abnormal Livers with Support Vector Machine Classification. Ultrasound Med Biol 46, 3379-3392 (2020).
Quiaoit K, et al. Quantitative ultrasound radiomics for therapy response monitoring in patients with locally advanced breast cancer: Multi-institutional study results. PloS one 15, e0236182 (2020).
Tufte ER. The visual display of quantitative information. Graphics Press (1997).
Baek J, et al. Principal components of ultrasound scattering enable the differentiation of steatotic and normal livers. Ultrasound Med Biol, (in review).
Jolliffe IT. Principal component analysis, 2nd edn. Springer (2002).
Jolliffe IT, Cadima J. Principal component analysis: a review and recent developments. Philos Trans A Math Phys Eng Sci 374, 20150202 (2016).
Cortes C, Vapnik V. Support-vector networks. Mach Learn 20, 273-297 (1995).
Vapnik VN. An overview of statistical learning theory. IEEE Trans Neural Networks 10, 988-999 (1999).
Bishop CM. Pattern recognition and machine learning, Chapter 7. Springer (2006).
Kuc R. Clinical application of an ultrasound attenuation coefficient estimation technique for liver pathology characterization. IEEE Trans Biomed Eng 27, 312-319 (1980).
Garra SB, Shawker TH, Insana MF, Wagner RF. In vivo attenuation measurement: methods and clinical relevance. Proceedings of the Sixth EC workshop, Paris Ultrasonic Tissue Characterisation 6, 87-100 (1986).
Parker KJ. Attenuation measurement uncertainties caused by speckle statistics. J Acoust Soc Am 80, 727-734 (1986).
Tada T, et al. Usefulness of Attenuation Imaging with an Ultrasound Scanner for the Evaluation of Hepatic Steatosis. Ultrasound Med Biol 45, 2679-2687 (2019).
Gong P, et al. Ultrasound Attenuation Estimation in Harmonic Imaging for Robust Fatty Liver Detection. Ultrasound Med Biol 46, 3080-3087 (2020).
Fukumura D, Jain RK. Tumor microvasculature and microenvironment: targets for antiangiogenesis and normalization. Microvasc Res 74, 72-84 (2007).
Mills BN, et al. Stereotactic body radiation and interleukin-12 combination therapy eradicates pancreatic tumors by repolarizing the immune microenvironment. Cell Rep 29, 406-421.e405 (2019).
Soares KC, et al. A preclinical murine model of hepatic metastases. J Vis Exp, 51677 (2014).
Dougherty G. Digital image processing for medical applications, p. 42. Cambridge University Press (2009).
Parker KJ, Baek J. Fine-tuning the H-scan for discriminating changes in tissue scatterers. Biomed Phys Eng Express 6, 045012 (2020).
Jayalakshmi T, Santhakumaran A. Statistical normalization and back propagation for classification. Int J Comput Theory Eng 3, 1793-8201 (2011).
Gary, R. Ge, Jannick P. Rolland, and Kevin J. Parker. "Speckle statistics of biological tissues in optical coherence tomography." Biomedical Optics Express 12.7 (2021): 4179-4191.
Luna, Antonio. Functional and Molecular Imaging in Oncology, An Issue of Magnetic Resonance Imaging Clinics of North America, E-Book. Vol. 24. No. 1. Elsevier Health Sciences, 2016.
Probability, Random Variables, and Stochastic Processes by A. Papoulis, McGraw-Hill, 1965.
J. Baek et al. Support Vector Machine (Svm) Based Liver Classification: Fibrosis, Steatosis, and Inflammation 2020 IEEE International Ultrasonics Symposium (Ius), IEEE, Sep. 7, 2020 (2020-09-07), pp. 1-4.

\* cited by examiner

METHOD OF USING MULTIPARAMETRIC IMAGING DATA TO DIAGNOSE DISEASE STATES AND TO MONITOR THEIR PROGRESSION

GOVERNMENT RIGHTS

This invention was made with government support under grant number EB025290 awarded by the National Institutes of Health. The government has certain rights in the invention.

BACKGROUND OF THE INVENTION

The invention relates to diagnostic medical imaging, and more particularly relates to diagnostic medical imaging using ultrasound. In its most immediate sense, the invention relates to the use of multiparametric imaging data to identify diseases and to monitor the progression of those diseases.

Liver fibrosis, liver steatosis ("fatty liver"), and liver metastasis are common human diseases. At present, diagnosis of these diseases is expensive, often very painful, and in some cases potentially harmful to the patient. Diagnosis of liver fibrosis and liver steatosis often requires a liver biopsy, which is very painful. Diagnosis of liver metastasis may require the use of PET-CT imaging and diagnosis of liver steatosis may require the use of MRI imaging. These technologies may require injection of imaging agents into the patient of imaging and these agents that can be contraindicated by unrelated patient conditions. For example, CT and MRI imaging agents can cause harm to patients who have kidney disease. And, technologies such as MRI and PET-CT are expensive.

Additionally, it is often painful and expensive to assess the progress of disease states. For example, determining the severity of a disease may require multiple biopsies or multiple expensive imaging studies.

Ultrasound imaging, on the other hand, is less expensive than technologies such as MRI and PET-CT, is painless, and does not require the use of surgery or imaging agents.

It would be advantageous to provide a method for diagnosing disease states—including but not limited to liver fibrosis, liver steatosis, and liver metastasis—that was not expensive, was not painful, and did not require surgical measures such as biopsies or injection of potentially harmful imaging agents into the patient. It would also be advantageous to provide a method for evaluating the progress of a disease without the need for such surgical measures or for multiple expensive imaging studies such as MRI and PET-CT. It would further be advantageous to provide a method for diagnosing disease states and monitoring disease progression using ultrasound imaging.

Accordingly, one object of the invention is to provide a method for diagnosing disease states and monitoring their progression without requiring surgical measures such as biopsies or injection of imaging agents, that is not painful, and that is not expensive.

Another object is to provide a method for diagnosing disease states and monitoring their progression using ultrasound imaging and multiparametric data from ultrasound imaging, MRI, and optical coherence tomography.

Still another object is, in general, to improve upon methods currently used in the art of diagnosing disease states and monitoring their progression.

SUMMARY OF THE INVENTION

The invention can be explained using results of experiments conducted using rodents. As is discussed in detail below, rats and mice were caused to develop liver fibrosis, liver steatosis, and liver metastasis and to undergo ultrasound imaging studies. Certain parameters of the resulting studies were then investigated. These experiments revealed that those parameters, when taken as an ensemble, were 100% successful at making differential diagnoses of these diseases, even though the parameters taken individually, have not been known to be useful in making such diagnoses. Furthermore, by monitoring the change in these parameters over time, it can be possible to not only to assess the progress of the disease, but indeed to diagnose the disease when other data are inconclusive.

In the course of conducting these successful experiments on rats and mice using multiparametric ultrasound imaging data relating to liver disease, the inventors realized that the methodology used in the experiments was more broadly useful and was limited neither to liver disease nor to the use of ultrasound as the imaging modality. Rather, the invention is applicable to e.g. magnetic resonance imaging data and optical coherence technology as well.

Thus, in accordance with the invention, an imaging modality is used to obtain measurements of a plurality of parameters. From changes in these parameters as a function of time, disease-specific trajectories are defined. Advantageously, these trajectories are color-coded, with different colors used to distinguish different parameters and progressively intense colorations used to show the progression of the parameter as a function of time.

Training sets provide the information necessary to analyze the diagnostic characteristics of the various disease states under investigation. The training sets are acquired by measuring the parameters of interest in vivo, using normal specimens and specimens in which the natures and states of development of the diseases of interest are known.

In the preferred embodiment described herein, the imaging modality used is ultrasound, but this is not required. Other modalities, such as magnetic resonance imaging and optical coherence tomography, can be used as well.

In accordance with a preferred embodiment of the invention, to diagnose a disease state in a volume of interest of a living subject using ultrasound imaging, a transducer is used to direct ultrasound pulses to the volume of interest and to receive RF echoes reflected from the volume of interest. The reflected RF echoes are analyzed to determine three categories of data:

1. the frequency domain transfer function of scatterers within the volume of interest; and
2. the propagation parameters of the ultrasound pulses within the volume of interest; and
3. the echo amplitude distribution within the volume of interest.

These data are then analyzed as an ensemble to diagnose the disease state.

In a preferred embodiment, the diagnosis is carried out by comparing results of the analysis against predetermined clusters of results that represent specific disease states, the comparison being carried out in a multi-dimensional parameter space. Optionally, and advantageously, the analysis is repeated to measure changes in the acquired data as a function of time. This makes it possible to evaluate the progress of the disease. And, such change can make it possible to diagnose the disease in instances where other data are inconclusive.

Also in accordance with a preferred embodiment of the invention, a method of diagnosing a disease state in a volume of interest of a living subject is disclosed. A transducer is used to direct ultrasound pulses to the volume of interest and the transducer is used to receive RF echoes reflected from the volume of interest.

The reflected RF echoes are analyzed to determine a physical characteristic of scatterers within the volume of interest, the acoustic attenuation within the volume of interest, and the distribution of echo amplitudes at the transducer. The determined physical characteristic, the determined acoustic attenuation, and the determined echo amplitudes are then used as an ensemble to diagnose the disease state.

In a preferred embodiment, the scatterers are cells and the determined physical characteristic is size. And in this preferred embodiment, the size of the cells is determined by computing the H-scan blue percentage of the reflected RF echoes. And, in the preferred embodiment, changes in acquired data as a function of time can be used for two purposes. The first purpose is to assess the severity of the disease and the rate at which it is progressing. The second purpose is to assist in identifying the particular disease state in instances wherein the acquired data are not definitive.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A preferred embodiment of the invention will be better understood with reference to the exemplary and non-limiting drawings, in which.

(b) Shows a flow chart suggesting liver diagnosis guide, including disease-specific imaging and 1D parameter method. First, clinicians would scan a liver and set ROI box. Then features are extracted using H-scan, attenuation estimation, and B-scan procedures. Using the measured features, trained support vector machines ("SVMs") identify liver conditions for all pixels within the ROI, and disease-specific imaging displays color images. Furthermore, using the features, 1D parameter analysis by trained SVM is also performed and help diagnosis based on H-scan trajectories in (c).

(c) Shows detailed color processing for disease-specific imaging. Input for the processing is features and CLASS from the SVM, which are obtained for all pixels within a ROI. A color for each pixel is assigned according to the determined CLASS, and then inner product between feature vector v and unit vector en for disease progression direction of the CLASS is performed to calculate color intensity. The unit vectors were also calculated when training SVM using all acquired frames in (a). The colors for PDAC tumor, fibrosis, and steatosis were set as red, green, and yellow, respectively. In this way, the color image is made and transparently overlaid on B-scan, whereas the pixels identified as normal do not have colors, showing only B-scan.

Figure 2:
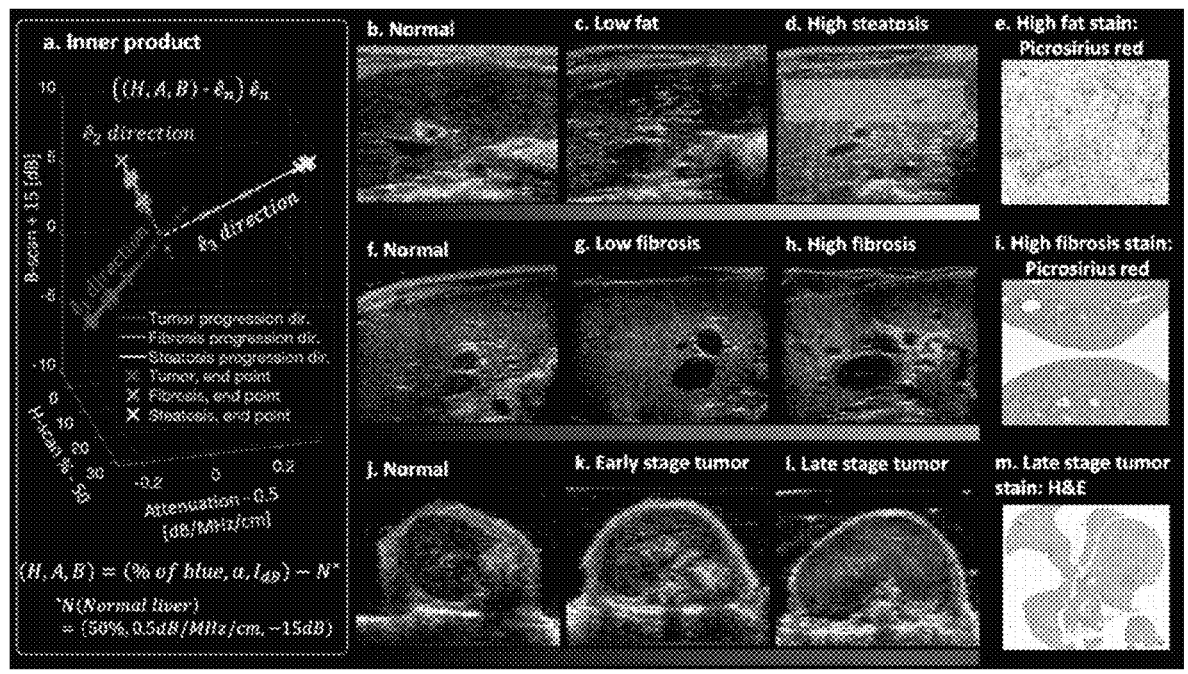

FIG. 2 Shows disease classification imaging. a. 3 features of liver tissues were extracted by H-scan, attenuation estimation, and B-scan, generating the components of (% blue, $\alpha, I_{dB}$), respectively. The coordinate represents (H,A,B)=(% blue,$\alpha,I_{dB}$)−(50,0.5,−15) for convenience, meaning changes from normal liver (50%,0.5 dB/MHz/cm,−15 dB). Linear lines show disease progression pathways from normal to end time point causing death. All measured features of this study were projected onto their disease' pathway, showing scatter plots. The end points causing death are denoted using the symbol "x". Then the distance between the origin and the measurement can be used for color intensity, meaning the greater value represent more severe disease. The SVM (support vector machine) classifies liver states, and assign colors of yellow, green, and red for steatosis, fibrosis, and tumor, respectively. Then, the colors are overlaid on B-scan (b-d, f-g, j-l). Normal in (b, f, j) only shows B-scan without colors. Early stages in (c, g, k) have some color area with low intensity. Late stages in (d, h, l) have full of color area with high intensity colors. Pathology slides (e, i, m) shows different cellular patterns for the three diseases, supporting the different colors for the three diseases.

Figure 3:
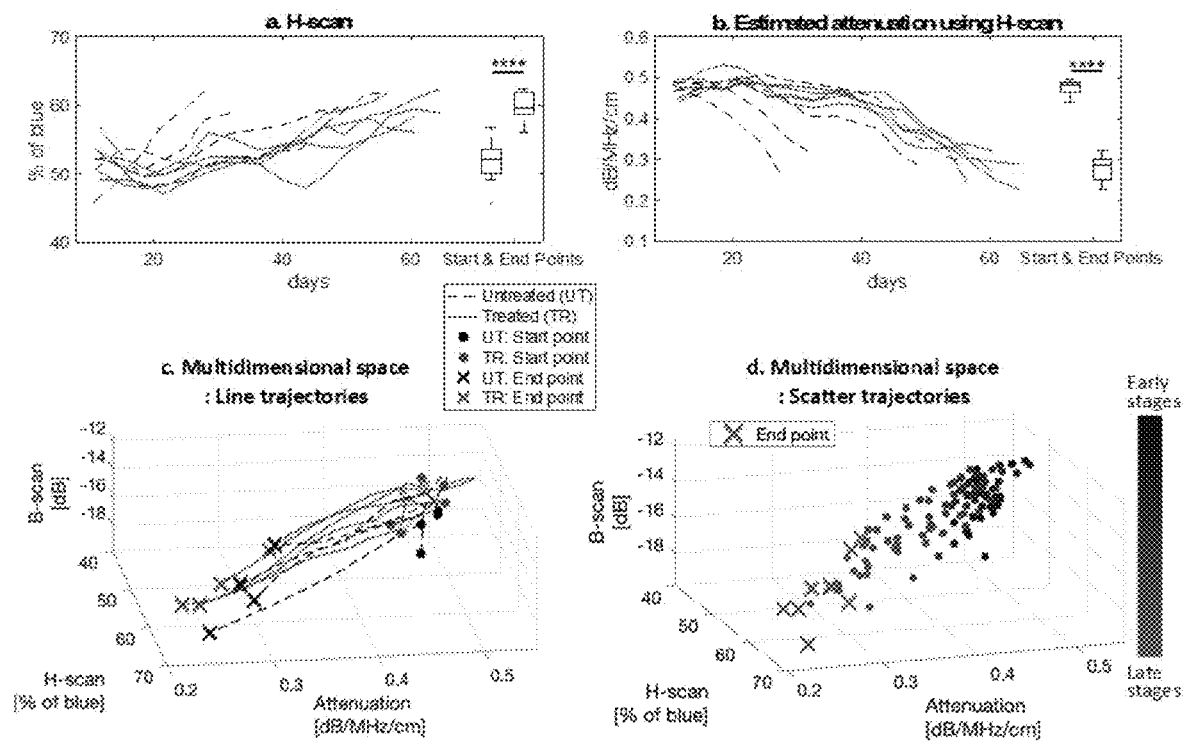

FIG. 3 Shows H-scan trajectories indicating the progression of PDAC tumor metastasis. H-scan analysis extracted two features within liver tissues which are blue percentage (a) and attenuation coefficient (b) along with time, representing days after tumor injection. The feature measurements were performed from start points (·) to end points (x), representing early and late stage causing death, respectively. The blue percentage (a) and attenuation (b) gradually increase and decrease over time, respectively, as tumor progresses. The features show significant between the early and late stages, and "****" denotes p-value<0.0001.

(c) A joint assessment of the two H-scan parameters and B-scan echo intensity in 3D parameter space, suggesting a pathway of tumor growth.

(d) Similar information as c) but with intermediate time points included. The gradual red colors from dark to bright represent early to late-stage tumors, which also demonstrates a tumor progression pathway.

Figure 4:
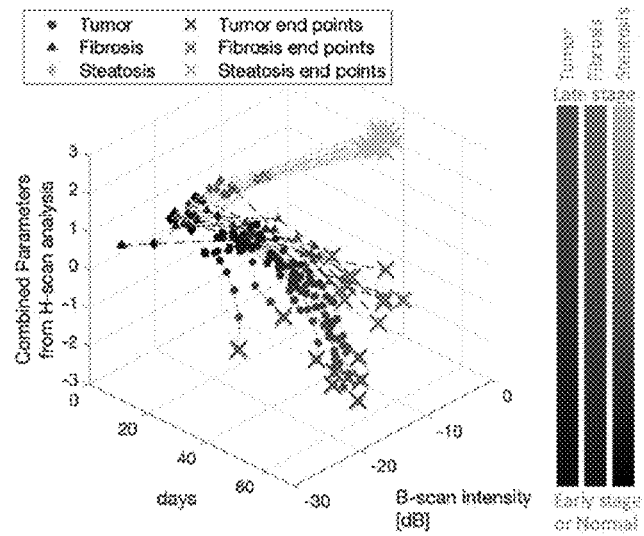

FIG. 4 Combining some measured parameters can be helpful to reduce the dimensionality such that a single 3D plot with time as one axis can demonstrate trajectories. Pathways showing disease progressions of steatosis, fibrosis, and PDAC metastases are shown in yellow, green, and red colors respectively. All of the three pathways are started from a position, (C,$I_{dB}$,time)=(0,−15, 0), representing normal or early stage diseases. They each end at different positions, showing clusters of the end point symbol "x".

Figure 5:
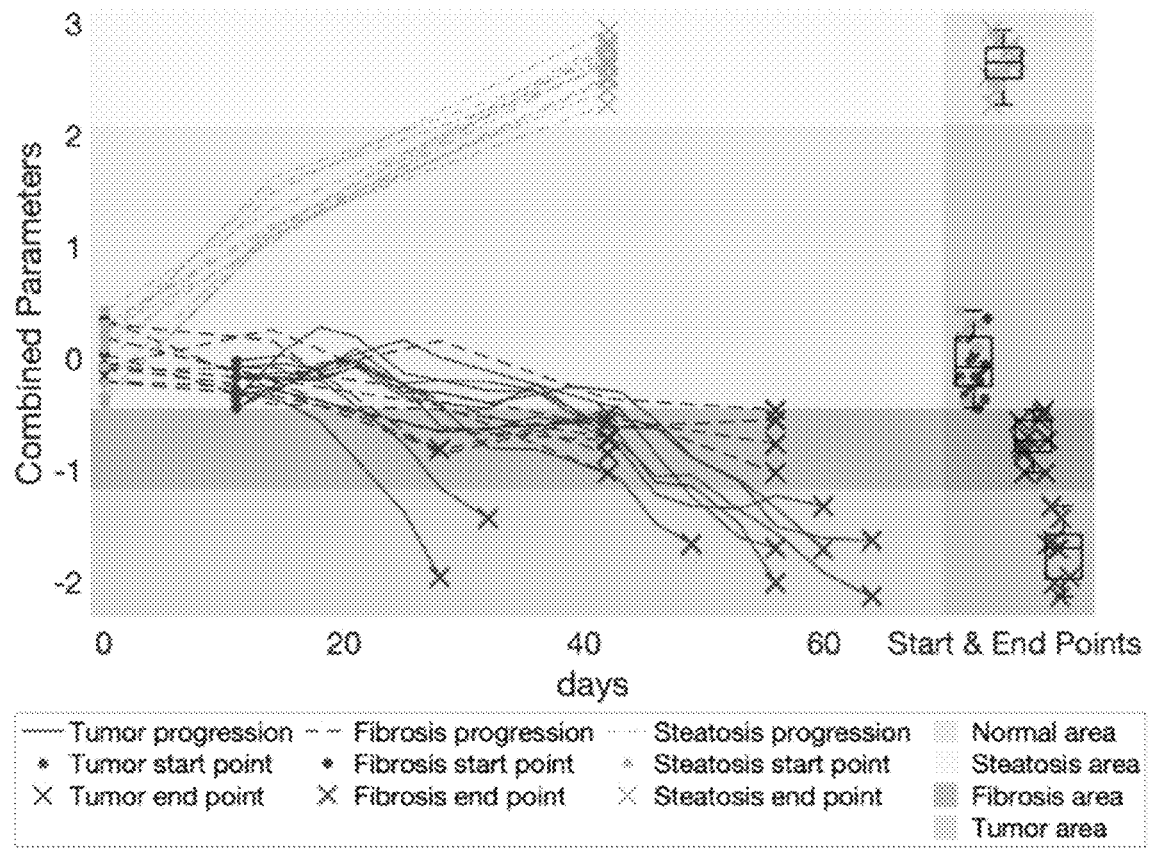

FIG. 5 Deriving a combined parameter creates a simplified interpretation of the trajectories of the three diseases: fibrosis, steatosis, and PDAC metastases. 1D SVM provides the diagnostic guideline based only on the combined parameters as the four-color area. Classification accuracy by the 1D SVM is 100% and the four groups are all statistically significant with p-value<0.0001.

Figure 6:
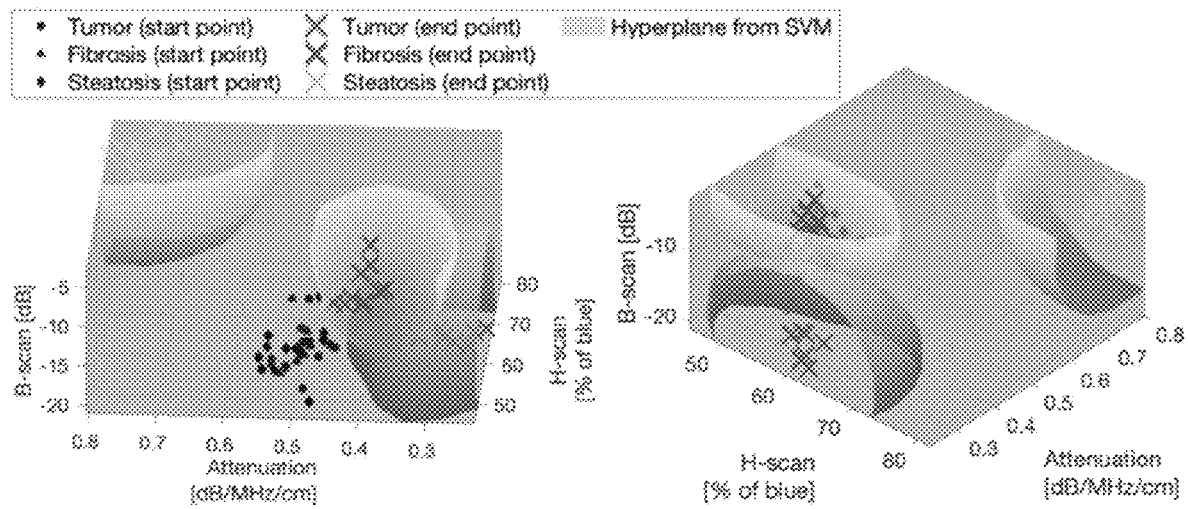

FIG. 6 Hyperplanes constructed by SVM. Normal, fibrosis, steatosis, and PDAC metastasis were well separated with 100% of classification accuracy. The original normal and endpoints of diseases are located within their hyperplane regions.

DETAILED DESCRIPTION OF PREFERRED EMBODIMENTS

The results of the herein-described experiments fall into two general categories. The first category is the use of ultrasound parameters to distinguish between three common diseases of the liver. The second category is the use of those ultrasound parameters to monitor and display the progress of a particular instance of a liver disease as a function of time.

The liver diseases investigated were liver fibrosis, liver steatosis, and pancreatic adenocarcinoma metastasis (herein referred to as "PDAC" metastasis), and the parameters were the H-scan blue percentage (% blue), the attenuation coefficient ($\alpha$), and the B-scan intensity in dB scale ($I_{dB}$) (all determined using "H-scan" analysis, a known analytical technique briefly discussed below). % blue relates to the upshift in scattering caused by scatterers (here, liver cells), $\alpha$ relates to the acoustic attenuation within the liver, and $I_{dB}$ relates to the B-scan echo intensity from regions inside the liver.

A. Experimental Methods and Data Acquisition a. Animal Models

Figure 1:
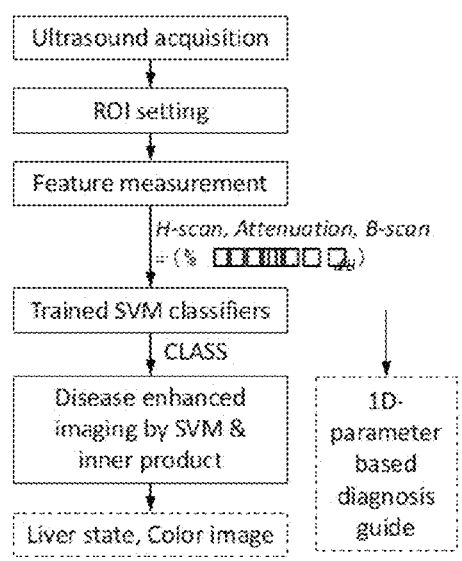
FIG. 1 (a) Summarizes study design and ultrasound acquisition. The three disease models were investigated and the number of enrolled animals for each model were provided. Three ultrasound scanners scanned the animals using the transmission beam types with their center frequencies ($f_c$). Each animal was scanned repeatedly over time to monitor disease progression, and for each scan, several frames were acquired, thereby the total of acquired frames are provided, and these were used for analyses of this study.
Figure 1:
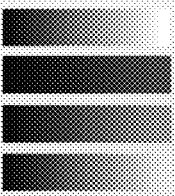

We investigated three diseases of PDAC liver metastasis, fibrosis, and steatosis as in vivo studies. This animal study is summarized in FIG. 1(a). The PDAC liver metastasis was developed in 9 mice (C57BL/6J) that were purchased from Jackson Laboratory (Bar Harbor, ME, USA). To grow the tumor in livers, 4×10^5 luciferase expressing murine pancreatic tumor cells (KCKO-luc) were injected into the spleen, and then the tumor cells spread through the hepatic veins, causing metastasis in the liver. The mice were divided into two groups of control (n=4) and treated (n=5). The treated group underwent chemotherapy with Gemcitabine (50 mg/kg dosing, twice per week). The tumor growth was confirmed by pathology and bioluminescence imaging (BLI). Hematoxylin and eosin (H&E) stained liver sections provided different colors for normal and tumor cells as shown in FIG. 2(m). According to BLI, all 9 enrolled mice showed an increase in radiance from D-Luciferin as the tumor grows. The PDAC study was approved by the University of Rochester Committee on Animal Resources.

The fibrosis was induced in response to carbon tetrachloride ($CCl_4$) exposure (1 mL/kg, three times per week) under approval of Pfizer Animal Care and Use Committee. Eleven rats were enrolled: 7 Sprague-Dawley (SD, Charles River Laboratories, Wilmington, MA, USA) and 4 TAC NIHRNU (nude, Taconic Biosciences, Inc., Rensselaer, NY, USA). After the $CCl_4$ dosing, an expert pathologist assessed fibrosis response using trichrome stain and Picrosirius red, and all the rats were graded as stage 4 fibrosis. However, since $CCl_4$ can also cause fat accumulation, we measured the fat area percentage by using Oil Red O stain, resulting in 2.9±1.9%. To verify the enrolled rats have fibrosis, but minimal fat accumulation, fat area for the other 9 normal SD rats was also measured, resulting in 1.2±1.5%: p-value comparing the normal and fibrosis group is 0.05.

Regarding the steatosis, a methionine and choline deficient (MCD) diet was employed to activate a nonalcoholic fatty liver disease (NAFLD) model. Twelve SD rats (Charles River Laboratories, Wilmington, MA, USA) were fed the MCD diet (MP Biomedicals, Solon, OH) for 6 weeks. The fat accumulation was assessed by a pathologist using Picro-Sirius red and H&E, demonstrating fat accumulation over time. The steatosis study was approved by the Institutional Animal Care and Use Committee (IACUC) at the University of Texas at Dallas.

b. Ultrasound Data Acquisition and Experimental Setup

Ultrasound scans were performed independently for the three disease models by using three different ultrasound systems; consequently, a total of 2778 ultrasound images were acquired as described in FIG. 1(a). First, a Verasonics ultrasound scanner (Vantage 256, Verasonics, Inc., Kirkland, WA, USA) equipped with an L11-5v probe at a 10 MHz center frequency imaged the livers with progression of the tumor. Plane wave transmission (25 angles, −6° to 6°) generated IQ data in the Verasonics system. For all 9 of enrolled mice for the PDAC tumor model, the data acquisition was performed twice a week from day 11 after the tumor cell injection until the death of each mouse; the last scan days range from day 28 to day 64. At each time point for the same mouse, 3 to 5 frames were obtained, resulting in 395 RF datapoints. The fibrosis study used a Vevo 2100 (FUJIFILM VisualSonics, Toronto, ON, Canada) with a 21 MHz center frequency linear array transducer (MS 250), of which focused beam transmission acquired RF data once a week from baseline before dosing; the rats survived until 6 or 8 weeks. At each time point for the same rat, approximately 30 frames were obtained, and therefore 1062 scans were acquired. The ultrasound scanner for the steatosis model is Vevo 3100 (FUJIFILM VisualSonics, Toronto, ON, Canada) utilizing a 15 MHz center frequency linear probe (MX 201). RF data acquisition with focused beam transmission was performed at baseline (before starting the MCD diet), week 2, and week 6. For each scan, approximately 30 frames were examined, resulting in 1337 scans.

Using the acquired ultrasound signals, we obtained B-mode images, and then set a ROI for each animal, including a consistent liver area over time for the same animal; example ROIs are provided in FIG. 2 (b-d, f-h, j-l) as the red boxes. The data within each ROI were assigned as inputs for H-scan, attenuation estimation, B-scan, and disease-specific imaging.

B. Feature Measurement

H-scan % blue, attenuation coefficient $\alpha$ (dB/MHz/cm), and B-scan intensity $I_{dB}$ (dB) were measured using H-scan matched filter analysis. H-scan matched filter analysis is a known analytical technique described in Parker K J, Baek J. Fine-tuning the H-scan for discriminating changes in tissue scatterers. *Biomed Phys Eng Express* 6, 045012 (2020). H-scan analysis reveals differences in transfer functions of scatterers and is implemented using convolution between ultrasound echo r(t) and a matched filter set, which can be n Hermite or n Gaussian filters $$\left\{ G_k \middle| \exp\left(-\frac{f - GC_k}{2\sigma_G^2}\right) \text{ for } k = 1, \ldots, n \right\}$$

with the Gaussian center frequencies $GC_k$, but the same band width $\sigma_G$. For each time point $$t, r(t) * \mathcal{F}^{-1}(G_k)$$

yields n convolution values that are likely to have a single maximum, indicating any shift in spectrum of the echo signal r(t) at the time t. Consequently, H-scan analysis can find the spectral shift at each sampling point of RF data by finding the maximum across the convolution results. However, ultrasound propagation causes frequency- and depth-dependent attenuation, resulting in the frequency down shift along with depth. The frequency shift was used to estimate the attenuation coefficient $\alpha$:

$$\alpha(x) = -\frac{f_p(x) - f_c}{x\sigma^2} \quad \text{[Equation (1)]}$$

where $f_p(x)$ is measured peak frequency (MHz) at depth x (cm). $f_c$ and $\sigma$ are the center frequency and band width of received echo, respectively, but before attenuation effects; these can be considered as initial parameters. With the estimated α, attenuation correction was performed, producing attenuation corrected signal r'(t). Convolution $$r'(t) * \mathcal{F}^{-1}(G_k)$$

then achieves matched filter outputs and corresponding peak frequencies for the points ∈(Sample,Scanline) again, and pseudocolor maps the frequency to H-scan color. Since each Gaussian filter has corresponding colors, there are n color levels ranging from red to blue. This study used n=256, indicating there are 256 color levels; the lower 128 levels from 1 to 128 in sequence represent red colors from vivid to darker, respectively, whereas the higher 128 levels from 129 to 256 represent from dark blue to vivid. Within the ROI of RF data, % blue is defined by:

$$\% \text{ blue} = \frac{(\text{number of blue pixels})}{(\text{number of total pixels})} \times 100\% \quad \text{[Equation (2)]}$$

More details for H-scan analysis including attenuation correction and attenuation estimation are found in the previously cited Parker and Baek paper, and in Baek J, Poul S S, Swanson T A, Tuthill T, Parker K J. Scattering Signatures of Normal versus Abnormal Livers with Support Vector Machine Classification. *Ultrasound Med Biol* 46, 3379-3392 (2020). respectively. The % blue varies according to Gaussian filter parameters of $GC_k$ and $\sigma_G$, and therefore we needed to set the parameters with a consistent standard for the three different ultrasound scanners. For the consistent setting, a band width (BW) is defined at 0.3 of normalized frequency spectrum S(f). Each scanner's $$\{GC_k | k=1 \ldots 256\}$$

of Gaussian filters was set to have % blue=50% for normal livers, and $$GC_{k=256} - GC_{k=1} = 0.7 \times BW$$

The three ultrasound scanners have different procedures to obtain log-compressed B-mode data, and the B-mode intensity was generally optimized for each scanner. Therefore, for use of B-scan intensity as a feature in addition to % blue and attenuation coefficient, the intensity of normal livers was set to −15 dB.

After measuring the features as described above using the 2778 ultrasound scans, the features at the same time point for the same animal were averaged, and therefore we finally obtained 115, 47, and 36 data set for PDAC tumor, fibrosis, and steatosis, respectively, meaning that a total of the 198 averaged data (% blue,α,$I_{dB}$) were used for all feature analysis.

While the preferred embodiment uses % blue, α, and $I_{dB}$ for all feature analysis, this is only preferred and is not necessary. Other parameters related to scattering and propagation can be used. While in this particular application (cancer classification in liver cells) H-scan analysis has been used to determine the frequency domain transfer function and particular propagation parameters of ultrasound echoes as well as particular distribution of echo amplitude within the volume of interest, this is not necessary. These characteristics can be determined by analyzing the reflected RF echoes using other statistical tools that are appropriate for the particular scatterers (in this preferred embodiment, liver cells are the scatterers) and environments (the liver, in this embodiment) in issue.

C. Training a Support Vector Machine ("SVM") and Using it to Distinguish Between Different Diseases a. Construction of a Combined Parameter C We proposed a non-linear transformation to produce a one-dimensional ("1D") parameter by combining two properties of principal component analysis ("PCA") and the features obtained by H-scan and attenuation estimation. We keep the form of transformation Z=XW from PCA where X and Z are the input and output of PCA, respectively, and W is a weight matrix, but we determine the W matrix based on the H-scan and attenuation results from livers. Normal livers are reported to have approximately 0.5 dB/MHz/cm attenuation and have 50% blue for H-scan measurement. When considering $$(\% \text{ blue},\alpha) \in \mathbb{R}^2$$

measurements from normal livers form clusters around (50, 0.5), and progression of any diseases makes the features (% blue,α) change from the normal values, following a pathway that is unique to the three studied diseases. The parameter changes of Δ(% blue) and Δα indicate the progressions; these two parameters are independently changed according to disease types.

Prior to parameter transformation, including PCA, data normalization is commonly performed such as Z-score or min-max normalization. To set zero-mean and unit-standard deviation, the normalized parameters $x_H$ and $x_A$ for % blue and α, respectively, are obtained by:

$$x_H = \frac{(\% \text{ blue}) - 50}{10}; x_A = (\alpha - 0.5) \times 10 \quad \text{[Equation (3)]}$$

where 50 and 0.5 are the averages of % blue and α, respectively, setting the zero-mean. The scaling operations by 10 serves to set approximately unit-standard deviation and also to set comparable scales for the two different measurements $x_H$ and $x_A$. Considering PCA with normalized parameters of $x_H$ and $x_A$, the first principal component $PC_1$ is:

$$PC_1 = w_1 \cdot x_H + w_2 \cdot x_A \quad \text{[Equation (4)]}$$

where $w_1$ and $w_2$ can be positive or negative and are optimized by PCA to maximize the variation of $PC_1$. However, after examining the way that PCA derives $PC_1$ from the two parameters in Equation (4) and the particular direction of changes with disease progression, we propose a Combined Parameter C:

$$C = w_H \cdot |x_H| + w_A \cdot |x_A| \quad \text{[Equation (5)]}$$

where $w_A = 0.6 \cdot \text{sign}(x_A)$ and $w_H = 0.4 \cdot \text{sign}(x_A)$. Note that both weights rely on the sign of attenuation, making this a nonlinear combination. The weights, 0.4 and 0.6, are optimized contributions from H-scan and attenuation, respectively, to maximize classification accuracy instead of the variance. Note that $w_H$ and $w_A$ can be positive or negative depending on the direction of change of attenuation, as $x_A$ is positive for steatosis but negative for fibrosis and PDAC metastases. Thus, the sign enables better discrimination between steatosis and the other two diseases. Therefore, the Combined Parameter C was used for a SVM training to classify liver states.

b. Using Combined Parameter C to Train a SVM

We trained two SVM classifiers using 32 animals with 4 liver states: normal, PDAC tumor, fibrosis, and steatosis. All 2778 ultrasound scans in this study were analyzed for values (% blue,$\alpha$,$I_{dB}$,C), and the features were averaged over frames for the same animal at the same time point, resulting in 198 feature sets for all time points. However, the SVM training used only 64 feature sets which were obtained only from the first and last scans, which are called start and end time points, respectively. The start points were considered as normal livers (n=32), and the end points became disease groups, including steatosis (n=12), fibrosis (n=11), and PDAC tumor (n=9), which were assigned as 4 classes.

SVM implementation was performed using MATLAB (The MathWorks, Inc., Natick, MA, USA). For the classification of the four classes, multiple vs. one method was used, and the Gaussian kernel function was also used to construct smooth hyperplanes. Hence the SVM learning involves the two parameters of box constraint and 2 of the Gaussian kernel, which were optimized to obtain robust hyperplanes, but avoiding overfitting; for the optimization, both hyperplane shapes and classification accuracies were observed by varying the two parameters.

Two SVM trainings were performed with one-dimensional ("1D") and three-dimensional ("3D") input features to suggest decision boundaries for trajectories based on parameters and images, respectively. When designing a liver diagnosis guide for clinicians with parameters, the simplest way can be providing decision boundaries for the 1D parameter which can be obtained repeatedly over time as the use of biparietal diameter. Therefore, with the 1D combined parameter, we first trained a 1D SVM classifier producing 1D decision boundaries for liver states.

Moreover, when we try to consider higher dimensional parameters with more information, such as 3D or M dimensions (M>3), showing trajectories in a 3D plot is not intuitively understandable or noticeable for 3D, and even impossible for M>3. However, M-dimensional measurements can describe the characteristics mathematically. Thus, we suggest a color imaging method with a 3D SVM classifier to effectively reveal and visualize disease trajectories with their decision boundaries; it is also applicable to M>3. The 3D SVM training requires data normalization to avoid weights for specific features caused by data scales. The scales of each component (% blue,$\alpha$,$I_{dB}$) differ in ranges of [0, 100], [0, 1], [−60, 0], respectively, but % blue and a hardly reach the extremes. (% blue,$\alpha \times 100$, $I_{dB}$) is likely to have comparable scales, which were therefore used for the 3D SVM training input and then produced 3D hyperplanes.

c. Displaying Disease Progression in Three Dimensions

We propose disease-specific imaging to consider higher-dimensional features and show their changes using gradual colors, which can effectively visualize 3D feature trajectories caused by disease progressions. A framework for the imaging methodology is provided in FIG. 1(b, c) and the following description: (1) Ultrasound data acquisition for a liver; (2) Feature measurements (% blue,$\alpha$,$I_{dB}$); (3) SVM classification for the input liver; (4) Color processing utilizing the SVM and inner product; (5) Display of disease-specific image, identifying the liver states.

When training the SVM, we also performed a pre-processing for the inner-product-based color processing to obtain pathways of disease progressions in 3D space. The SVM trainings used 64 data at start and end time points, whereas the inner product operation employed features at all time points, consisting of 198 data of $$(\% \text{ blue},\alpha,I_{dB}) \in \mathbb{R}^3$$

Using the 3D features, we define a vector v suggesting disease progression directions starting from a position N of normal liver:

$$v=(H,A,B)=(\% \text{ blue},\alpha,I_{dB})-N \qquad \text{[Equation (6)]}$$

where N=(50%,0.5 dB/MHz/cm, −15 dB), and each component of (H,A,B) represents feature changes from normal. When monitoring the vector v of a liver from normal state until any disease progresses, v starts from the origin of O=v=(0,0,0) and repeated measurements over time move gradually further from the origin O. Then, the trajectories of v indicate disease progression pathways and also directions of progression. By collecting v for each disease, linear pathways of tumor, fibrosis, and steatosis can be obtained by linear fittings; the lines are shown in FIG. 2(a). Furthermore, the progression directions for tumor, fibrosis, and steatosis can be also estimated by calculating unit vectors of $\hat{e}_1$, $\hat{e}_2$, and $\hat{e}_3$, respectively. Then, an inner product given by $$v \cdot \hat{e}_n$$

indicates progression of n-th disease, and the values calculated from $$v \cdot \hat{e}_n$$

for all enrolled 198 data are exhibited in FIG. 2(a) as points with colors representing disease stages: the darker and brighter colors represent early and late stages of each disease, respectively, until the time of death given by the symbol "x". Among the 198 projections onto the linear pathways, maximum values of the diseases were obtained:

$$\text{maxTumor}=\max(v \cdot \hat{e}_1), \text{maxFib}=\max(v \cdot \hat{e}_2)$$

for tumor, fibrosis, and steatosis, respectively. The maximum values are used to normalize the inner product results, and then as described in FIG. 1(c), the normalized values of $$\frac{\langle v, \hat{e}_n \rangle}{\max(Disease)_n}$$

are assigned for RGB color intensity for each pixel, wherein v is a measurement from any pixels within the ROI and the disease index of n is determined by the classification result of the trained 3D SVM. The normalized value utilizing inner product and SVM indicates disease progression; the higher the value, the more severe the disease, but a value near 0 indicates normal or early stage. In this way, a color image is processed, and then overlaid with its B-scan image; pixels classified as normal only display B-scan without color overlay.

D. Visual Display of Disease Progression

Perhaps the most simple and traditional approach for illustrating disease progression is measuring and plotting each measured parameter individually over time. For example, the progression of PDAC liver metastasis was investigated by analyzing radiofrequency (RF) echoes, and consequently the H-scan measures provided measurement changes over time in days, indicating the tumor growth as shown in FIG. 3. For example the percent (%) of blue parameter in FIG. 3(a), shows a gradual increase over time for both of untreated and treated (with chemotherapy) mice, but chemotherapy group tends to have an increase in survival compared to the untreated group. When considering only start and end points, the percent difference is significantly different with p-value of 5.7×10-6. Moreover, we estimated the attenuation coefficient using the H-scan approach by measuring frequency down shift along with depth, and FIG. 3(b) demonstrates that the attenuation coefficient can decrease with gradual tumor growth over time. The start and end points show significant difference (p-value=3.6×10-10) without any overlap between the measurements of the two groups. Whereas, the difference between the start and end points investigated by traditionally used B-scan intensity has a p-value of 0.01, which is statistically significant, but the p-value is greater than that of H-scan % blue or the attenuation coefficient. Thus, H-scan % blue and attenuation estimation more sensitively describe the changes induced by the tumor compared to B-scan. In FIG. 3(c,d), we combine the three metrics to make a joint assessment of the three, and therefore considered three dimensional (3D) features for each liver and time point, (% blue,$\alpha$,$I_{dB}$). The gradually changed red colors from dark to bright red in FIG. 3(d) illustrate start-to-end time points, representing liver changes from normal to an end-stage metastatic condition causing death. The trajectories in the plot of FIG. 3(c) suggest a common pathway of tumor growth. To be specific, scatterers with features (% blue,$\alpha$, $I_{dB}$) located near front left can be considered as late stage tumor.

Unfortunately, 3D data are best appreciated with the assistance of an interactive graphics tool and 3D displays. However, in many studies we have more than three measured parameters. In these cases, we cannot directly visualize a higher multidimensional space, and so require a strategy for reducing these. From mathematics, we have a number of options, including simple projections from M dimensional space to 3D or 2D representations, or data-specific techniques such as PCAs. These are linear operations; however nonlinear transformations may be more revealing. To illustrate this effect, we show the 3 parameter measurements (% blue,$\alpha$,$I_{dB}$) vs time (strictly requiring a 4D display) on the different classes of diseases from independent studies of liver fibrosis, steatosis, and PDAC metastases. To reduce the dimensionality, we applied a nonlinear transformation to obtain the Combined Parameter C, related to the distance in 2D from the center of the "normal" cluster defined in Equation (5). The reduced parameters of C, $I_{dB}$, and time are shown in FIG. 4, suggesting the three distinct pathways of fibrosis, steatosis, and PDAC metastases over time. In practice, when monitoring a liver over time whose condition has not been pathologically confirmed, measuring (C,$I_{dB}$,time) and then determining the most similar pathway of known classes of pathology can help clinicians diagnose the liver's condition.

While this is comprehensive, it is difficult for clinicians to examine and interpret patient data in this form without the help of an interactive 3D display. However, reducing the dimensionality to one combined parameter vs. time is simpler and is compatible with hard copies of reports. The nonlinear mapping creating the Combined Parameter C can be related to the distance in 2D from the center of the "normal" cluster, and creates a simplified interpretation of the trajectories that can be used clinically to assess the progress of any individual liver with any of these three conditions as shown in FIG. 5. In this combined parameter plot vs. time, each disease has its own trajectory describing the changes of its tissue characteristics, and its end points formed clusters along the 1D axis of the Combined Parameter C. Accordingly, by using the end points of the three diseases in addition to the start points of all as a normal group, the four groups were used for 1D SVM training, producing 1D decision boundaries to differentiate the liver conditions: normal, fibrosis, steatosis, and PDAC metastases. The 1D classification accuracy is 100% without any overlap between the four groups. The four liver conditions were depicted using black, green, yellow, and red corresponding to normal, fibrosis, steatosis, and PDAC metastases, respectively. Hence, when a liver has a Combined Parameter C calculated from H-scan and attenuation estimation, clinicians may assess the progression of disease states based on mapping a particular patient's information over time.

E. Use of a Support Vector Machine to Generate Clusters Demonstrating Differentiation Between Normal, Fibrotic, Steatotic, and Metastatic Regions Measurements in multidimensional space are provided in FIG. 6, involving analysis of clusters, one effective means for this is the SVM. Hyperplanes can be created by the SVM in the 3-parameter (% blue,$\alpha$,$I_{dB}$) space as shown in FIG. 6. The SVM including the hyperplanes is also employed for disease-specific imaging.

These hyperplanes can discriminate the three studied conditions with 100% accuracy. Furthermore, they define regions in M-dimensional spaces (for M measured parameters) associated with specific diseases. The trajectory of an individual with progressive disease, scanned repeatedly over time, may approach one of these clusters. When monitoring a liver growing any of the diseases, the trajectory starts from the normal cluster that has a center at 50% of H-scan, 0.5 dB/MHz/cm of attenuation coefficient, and a standardized −15 dB of B-scan intensity, denoting (50, 0.5, −15) in the 3D space. As the disease progresses, the trajectory reaches one of the hyperplane boundaries defined by SVM, and then the trajectory goes further into the disease region, whereby the distance between the last measurement (% blue,$\alpha$,$I_{dB}$) and the center (50, 0.5, −15) of the normal cluster is getting longer. The distance can be correlated with the vector (H,A,B)=(% blue,$\alpha$,$I_{dB}$)−(50, 0.5,−15).

As can be seen in FIG. 6, the disease state of liver metastasis is diagnosed when the cells and scattering structures are moderately small (H-scan % blue values from approximately 60% to approximately 70%), the acoustic attenuation is low (a values from approximately 0.2 to approximately 0.3 dB/cm/MHz), and the echo amplitude is low to moderate ($I_{dB}$ values from approximately −15 to approximately −20 dB). The disease state of liver fibrosis is diagnosed when the cells and scattering structures are slightly large (H-scan % blue values from approximately 50% to approximately 60%), the acoustic attenuation is moderate (a values from approximately 0.35 to approximately 0.45 dB/cm/MHz), and the echo amplitude is high ($I_{dB}$ values from approximately −10 to approximately 0 dB). The disease state of liver steatosis is diagnosed when the cells and scattering structures are small (H-scan % blue values from approximately 70% to approximately 80%), the acoustic attenuation is high (a values from approximately 0.65 to approximately 0.8 dB/cm/MHz), and the echo amplitude is high ($I_{dB}$ values from approximately −5 to approximately −15 dB/cm/MHz).

For disease-specific imaging, this phenomenon can be interpreted by using inner product operation. First, linear paths from the center to end points are provided in FIG. 2(a); the three solid lines represent the central pathways of the diseases. With the (H,A,B), we obtained the projections (a dot product in vector space) onto the paths, and the projections are shown as a scatter plot in FIG. 2(a). The dark to bright colors correspond to progressively later stages. The earlier measurements were seen near the origin (0,0,0), and as the disease grows, the bright colors became further from the origin. By using the gradual increase in projection values caused by disease progressions, B-scan images can therefore be enhanced with the color intensity determined by the projection values. Examples of disease-specific imaging are displayed in FIG. 2(b-d), (f-h), and (j-l). The top row shows fat growth with increase in yellow color. Similarly, the mid and bottom rows show fibrosis and tumor growth with increase in green and red colors, respectively. The diseases are progressive from left to right for the same animal, but scanned repeatedly three times. The hyperplanes shown in FIG. 6 identified a liver state of each pixel, and colors were assigned according to the identified disease type: yellow, green, and red for steatosis, fibrosis, and PDAC metastasis, respectively. Lastly, the projection operation determined the color intensity of the pixels. In this approach, the more severe the disease, the more vivid the color. Therefore, all the pixels at the earliest time points in FIG. 2(b, f, j) do not have colors, meaning that all the pixels were classified as normal without any disease. The given cases at mid time points in FIG. 2(c, g, k), have some color enhanced pixels, but these are darker than the colors at end time points in FIG. 2(d, h, l). The final scans show nearly complete fill in with saturated colors, meaning the pathologies were distributed throughout the entire regions of interest (ROI). FIG. 2(e, i, m) are histology images of the three disease models showing different liver compositions and patterns, which supports the three different colors for the disease models. In this framework, clinicians can assess disease based on the color enhancement, and moreover they can infer the severity and extent of the diseases based on color intensities. While scanning the liver repeatedly over time, they also can track the disease progression wherein gradual increase in color intensities.

F. Conclusion

The herein-disclosed preferred embodiment enables an assessment of disease progression by combining two major steps: defining multidimensional parameter trajectories that are disease-specific, and applying color-enhanced imaging representing the parameters' gradual changes. One simple trajectory results from the combined parameter C derived from H-scan analyses and provides a useful tool for diagnosis or staging of the three conditions. H-scan trajectories track the disease progression more sensitively as compared to other ultrasound imaging methods such as B-scan or shear wave elastography (SWE). Furthermore, H-scan yielded better performance than the recently used ultrasound application of SWE to detect early-stage tumors. Moreover, in addition to the high performance of H-scan analysis, another important aspect for differential diagnosis is finding well-separated measurement clusters representing different liver conditions. The combined parameter C achieved 100% classification accuracy without any overlap according to SVM classification and thus can provide a differential diagnosis between the three conditions of the liver. For visualization, the gradual changes of the H-scan parameters are converted to color intensities with reference to the multiparametric clusters and then the colors are transparently overlaid on B-scan images. The multidimensional parameters are efficiently mapped into the color spaces by SVM and the inner product. Hence, the colors for diseases show up more vividly as the diseases become severe, potentially aiding clinicians in tracking the disease progression.

This study enrolled three disease models and their livers were independently scanned by three ultrasound systems with different scan conditions such as different transducers, signal processing procedures, and parameter settings. H-scan analysis was used to investigate their ultrasound echoes and resulted in meaningful features, identifying liver tissues' characteristics of attenuation and structure provided by a (dB/MHz/cm) and % blue, respectively. There has been long history of researches in measuring attenuation coefficient $\alpha$, employing traditional or currently developed methods. Our H-scan analysis of attenuation within the three liver diseases of metastatic tumor, fibrosis, and steatosis showed consistent $\alpha$ with the previous studies. For normal, $\alpha=0.5$ dB/MHz/cm, steatosis has higher a (>0.726, this study $\alpha=0.74\pm0.04$ dB/MHz/cm) than normal, and fibrosis was reported to have less than $\alpha=0.4525$, 26 (this study $\alpha=0.40\pm0.02$ dB/MHz/cm). Regarding the metastatic tumor model, estimated attenuation ($\alpha=0.30\pm0.04$ dB/MHz/cm) is less than the normal and could be due to leaky tumor vessels and increase in fluid.

We verified the enhanced imaging by investigating endpoints' histology figures (FIG. 6). Since the liver patterns in histology show widespread abnormal tissues in each case, a filling-in of colors within ROIs can be considered as correct results. Furthermore, the gradual increase or decrease in the measured parameters in FIGS. 2-4 was observed, whereby the gradual increase in color area and intensity in FIG. 6 also appears correct. Particularly, FIG. 6 has two types of regions of B-scan-only and color-overlaid area, suggesting normal and diseased regions, respectively.

The methodology including 1D diagnosis trajectory and disease-specific imaging was performed using the three H-scan outputs. However, the approach can be extended to employ more parameters (M>3). For instance, there are methods producing several parameters, such as SWE and histogram analysis. Let assume we have M parameters generated by H-scan, B-scan, SWE, Burr, and more methods, then PCA or nonlinear transformation can reduce the number of parameters, suggesting 1D parameter for diagnosis guide. Regarding the disease-specific imaging, PCA can reduce the parameters into three principal components, and then the resulting methodology is the same as with this study. Otherwise, the M parameters can be directly used for the imaging since SVM and inner product works for M-dimensional input. Examples of multiparametric analysis (M>3) utilizing PCA and SVM are found in previous studies (Baek J, Poul S S, Swanson T A, Tuthill T, Parker K J. Scattering Signatures of Normal versus Abnormal Livers with Support Vector Machine Classification. *Ultrasound Med Biol* 46, 3379-3392 (2020), Baek J. et al. Principal components of ultrasound scattering enable the differentiation of steatotic and normal livers. *Ultrasound Med. Biol*, (in review). Significantly, once a training set of images has been acquired, it may not be necessary to repeatedly image the subject under investigation. Depending upon the disease(s) involved and the state(s) of their progression, the parameter values produced during only one imaging step may be adequate for diagnostic purposes. However, if this is not adequate, the subject can be imaged repeatedly, and a trajectory formed from the results, making it possible to compare a trajectory formed from the subject under investigation to the trajectories formed from the training set of images.

Furthermore, once an appropriate training set of images has been acquired, it may not be necessary to re-acquire it. The information from the training set can be stored and reused as necessary.

One limitation of the rodent study is that three distinct disease models were analyzed, however in clinical practice a patient can present with a combination of pathologies, for example fibrosis plus steatosis plus metastases plus other possible abnormalities.

To use the H-scan trajectory approach clinically in commercial ultrasound scanners, a simple protocol for clinicians and the possibility of real-time processing would be advantageous. Once users set an ROI box similar to the color Doppler scan, the rest of scanning procedure is the same as a conventional B-scan. Additionally, when considering implementation on ultrasound devices, there is no requirement for additional or altered transmit or receive sequences, whereas Doppler modes or SWE require their own transmit, receive, and process sequences.

To summarize, the H-scan analysis in the preferred embodiment enables accurate quantification of ultrasound signals, and then its multiple parameters (along with other available parameters such as shear wave speed or contrast related measures) can be efficiently unified by parameter transformation, SVM, and inner product. Consequently, H-scan trajectories assess the progression of pathologies using a single combined parameter over time, and through enhanced imaging with color overlays on B-scan derived from SVM clusters specific to disease states. These approaches resulted in 100% accuracies, classifying normal liver, PDAC metastasis, fibrosis, and steatosis within a unified framework. We anticipate clinical use of these methods since they achieved the high performance and can be implemented in real-time.

One of ordinary skill in the art will recognize that there are other organs and tissues that have ultrasound echoes and can be affected by diseases. Furthermore, one of ordinary skill in the art who had read the classic textbook "Probability, Random Variables, and Stochastic Processes" by A. Papoulis, McGraw-Hill, 1965, would recognize that the ultrasound echo properties described herein in the preferred embodiment can be derived by other substantially equivalent mathematical techniques. Specifically, the echo RF, amplitude, and spectral levels can all be quantified using the methods of signal processing, probability, random variables, and stochastic properties to quantify the statistical properties.

Also, the propagation of the ultrasound and transverse waves through the tissue is, in classical physics terms, characterized by a wavenumber with real and imaginary parts corresponding to the speed of sound and attenuation coefficient, respectively. We call these, generally, the propagation parameters. Our multi-parameter framework for assessing the trajectories of diseases applies directly to pluralities of statistical parameters and propagation parameters.

As has been stated above, although the presently preferred embodiment of the invention uses ultrasound as the imaging modality of choice, this is not required. For example, if the magnetic resonance imaging modality is chosen, the trajectories can be formed using proton weighted density data, T1 and T2 weighted data, fat weighted data acquired using special sequences, etc. Alternatively, if the optical coherence tomography modality is chosen, the trajectories can be formed using optical attenuation, optical speckle distribution, and optical scattering strength.

Such multiparametric measures can be analyzed within the above-described framework of defining multidimensional parameter trajectories that are disease-specific, and applying color-enhanced imaging representing the parameters' gradual changes.

For example, within the magnetic resonance imaging modality, a number of measures are well established output parameters from clinical scanners and are known to change progressively with different diseases of the liver, brain, prostate, and other organs. These parameters include, but are not limited to, proton weighted density data, T1 and T2 weighted data, measures of contrast uptake and washout, diffusion weighted data, spectroscopic data, tissue stiffness data, and fat weighted data from special sequences. (Luna, Antonio. *Functional and Molecular Imaging in Oncology, An Issue of Magnetic Resonance Imaging Clinics of North America, E-Book*. Vol. 24. No. 1. Elsevier Health Sciences, 2016.)

For another example, in optical coherence tomography there are well known measures that can change with tissue types and disease states. These include optical attenuation, optical speckle distribution, and optical scattering strength. (Gary, R. Ge, Jannick P. Rolland, and Kevin J. Parker. "Speckle statistics of biological tissues in optical coherence tomography." *Biomedical Optics Express* 12.7 (2021): 4179-4191.)

To analyze these MRI and OCT multiparametric measures within our framework of defining multidimensional parameter trajectories, one first obtains data from a training set of normal and selected disease states. The multi-parametric data obtained are then assessed in plots of multi-dimensional parameter space to find clusters representing different conditions, as shown in FIG. 6, and following the steps in previous section C) "Training a Support Vector Machine ("SVM") and Using It to Distinguish Between Different Diseases". From this point, patient data can be analyzed and displayed with color intensity overlay using the inner product mathematics described in FIG. 2 and in section D) "Visual Display of Disease Progression"

In this way, the colors representing selected diseases show up more vividly as the diseases become severe, potentially aiding clinicians in tracking the disease progression, and thereby increasing the utility of the ultrasound, MRI, and OCT images by incorporating the multiparametric data within the herein-disclosed analysis framework.

Although a preferred embodiment has been described above, the invention is limited only by the following claims:

The invention claimed is:

1. A method of diagnosing a disease state in a volume of interest of a living subject, comprising the following steps:
   a. using a transducer to direct ultrasound pulses to the volume of interest;
   b. using the transducer to receive RF echoes reflected from the volume of interest;
   c. analyzing the reflected RF echoes to determine
      i. a physical characteristic of scatterers within the volume of interest, wherein the scatterers are cells, and
      ii. the acoustic attenuation within the volume of interest, and
      iii. the echo amplitude; and
   d. using the determined physical characteristic, the determined acoustic attenuation, and the determined echo amplitude to diagnose the disease state;
   wherein the disease state is liver metastasis; and
   wherein the disease state of liver metastasis is diagnosed when the cells have H-scan % blue values from 60% to 70%, the acoustic attenuation has $\alpha$ values from 0.2 to 0.3 dB/cm/MHz, and the echo amplitude has $I_{dB}$ values from −15 to −20 dB.

2. A method of diagnosing a disease state in a volume of interest of a living subject, comprising the following steps:

a. using a transducer to direct ultrasound pulses to the volume interest;
b. using the transducer to receive RF echoes reflected from the volume of interest;
c. analyzing the reflected RF echoes to determine
   i. a physical characteristic of scatterers within the volume of interest, wherein the scatterers are cells, and
   ii. the acoustic attenuation within the volume of interest, and
   iii. the echo amplitude; and
d. using the determined physical characteristic, the determined acoustic attenuation, and the determined echo amplitude to diagnose the disease state;
wherein the disease state is liver fibrosis; and
wherein the disease state of liver fibrosis is diagnosed when the cells have H-scan % blue values from 50% to 60%, the acoustic attenuation has α values from 0.35 to 0.45 dB/cm/MHz, and the echo amplitude has $I_{dB}$ values from −10 to 0 dB.

3. A method of diagnosing a disease state in a volume of interest of a living subject, comprising the following steps:
a. using a transducer to direct ultrasound pulses to the volume of interest;
b. using the transducer to receive RF echoes reflected from the volume of interest;
c. analyzing the reflected RF echoes to determine
   i. a physical characteristic of scatterers within the volume of interest, wherein the scatterers are cells, and
   ii. the acoustic attenuation within the volume of interest, and
   iii. the echo amplitude; and
d. using the determined physical characteristic, the determined acoustic attenuation, and the determined echo amplitude to diagnose the disease state;
wherein the disease state is liver steatosis; and
wherein the disease state of liver steatosis is diagnosed when the cells have H-scan % blue values from 70% to 80%, the acoustic attenuation has a values from 0.65 to 0.8 dB/cm/MHz, and the echo amplitude has Ids values from −5 to −15 dB/cm/MHz.

4. A method of diagnosing a disease state in a volume of interest of a living subject, comprising the following steps:
a. using a transducer to direct ultrasound pulses to the volume of interest;
b. using the transducer to receive RF echoes reflected from the volume of interest;
c. analyzing the reflected RF echoes to determine
   i. a physical characteristic of scatterers within the volume of interest, wherein the scatterers are cells, and
   ii. the acoustic attenuation within the volume of interest, and
   iii. the echo amplitude; and
d. using the determined physical characteristic, the determined acoustic attenuation, and the determined echo amplitude to diagnose the disease state;
wherein the disease state is diagnosed when the cells have H-scan % blue values above 50%, the acoustic attenuation has α values below or above 0.5 dB/cm/MHz, and the echo amplitude has $I_{dB}$ values below or above −15 dB in relation to a center of a normal cluster of cells in three-dimensional space.

5. The method of claim 4, wherein the disease state is liver metastasis and wherein the disease state is diagnosed when the cells have H-scan % blue values above 50%, the acoustic attenuation has α values below 0.5 dB/cm/MHz, and the echo amplitude has $I_{dB}$ values below −15 dB in relation to a center of a normal cluster of cells in three-dimensional space.

6. The method of claim 4, wherein the disease state is liver fibrosis and wherein the disease state is diagnosed when the cells have H-scan blue values above 50%, the acoustic attenuation has α values below 0.5 dB/cm/MHz, and the echo amplitude has $I_{dB}$ values above −15 dB in relation to a center of a normal cluster of cells in three-dimensional space.

7. The method of claim 4, wherein the disease state is liver steatosis and wherein the disease state is diagnosed when the cells have H-scan % blue values above 50%, the acoustic attenuation has α values above 0.5 dB/cm/MHz, and the echo amplitude has $I_{dB}$ values above −15 dB in relation to a center of a normal cluster of cells in three-dimensional space.

* * * * *